United States Patent
de Wilde

(10) Patent No.: US 12,245,992 B2
(45) Date of Patent: **\*Mar. 11, 2025**

(54) METHOD FOR SUPPORTING MEMORY FUNCTION AND/OR COGNITIVE FUNCTION

(71) Applicant: N.V. Nutricia, Zoetermeer (NL)

(72) Inventor: Mattheus Cornelis de Wilde, Utrecht (NL)

(73) Assignee: N.V. Nutricia, Zoetermeer (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/419,590

(22) Filed: Jan. 23, 2024

(65) Prior Publication Data
US 2024/0156748 A1    May 16, 2024

Related U.S. Application Data

(62) Division of application No. 17/399,160, filed on Aug. 11, 2021, now Pat. No. 11,918,546, which is a division of application No. 16/083,399, filed as application No. PCT/NL2017/050140 on Mar. 8, 2017, now Pat. No. 11,123,306.

(30) Foreign Application Priority Data

Mar. 8, 2016 (WO) ................ PCT/NL2016/050161

(51) Int. Cl.
*A61K 31/04* (2006.01)
*A61K 31/202* (2006.01)
*A61K 31/375* (2006.01)
*A61K 31/7068* (2006.01)
*A61K 31/7072* (2006.01)

(52) U.S. Cl.
CPC ............ *A61K 31/04* (2013.01); *A61K 31/202* (2013.01); *A61K 31/375* (2013.01); *A61K 31/7068* (2013.01); *A61K 31/7072* (2013.01); *A61K 2300/00* (2013.01)

(58) Field of Classification Search
CPC .... A61K 31/04; A61K 31/202; A61K 31/375; A61K 31/7072; A61K 2300/00; A61K 31/7068; A61P 3/02; A61P 25/28
See application file for complete search history.

(56) References Cited

U.S. PATENT DOCUMENTS

| | | |
|---|---|---|
| 8,076,282 B2 | 12/2011 | Hageman |
| 8,361,989 B2 | 1/2013 | Groenendijk et al. |
| 8,362,078 B2 | 1/2013 | Kiliaan et al. |
| 2015/0044138 A1* | 2/2015 | Lansbergen ........... A61K 49/22 424/9.2 |

FOREIGN PATENT DOCUMENTS

| | | |
|---|---|---|
| WO | 02/088129 | 11/2002 |
| WO | 2006/127620 | 11/2006 |
| WO | 2007/073177 | 6/2007 |
| WO | 2009/002148 | 12/2008 |
| WO | 2009/002165 | 12/2008 |
| WO | 2012/125034 | 9/2012 |
| WO | 2013/066152 | 5/2013 |
| WO | 2013/129914 | 9/2013 |
| WO | 2013/129931 | 9/2013 |
| WO | 2013/149384 | 10/2013 |
| WO | 2015/140545 | 9/2015 |
| WO | 2016/083362 | 6/2016 |

OTHER PUBLICATIONS

Steinbrenner et al: "Selenium homeostasis and selenoproteins in brain: implications for disorders in the central nervous system", Archives of Biochemistry and Biophysics, 536 (2013), pp. 152-157.
"Abstracts", Journal of Neurological Sciences, Elsevier Scientific Publishing Co., Amsterdam, NL, vol. 229-230, Mar. 15, 2005, pp. 293-384.
Kishi et al: "Protection against Brain Atrophy by Ant-dementia Medication in Mild Cognitive Impairment and Alzheimer's Disease: Meta-Analysis of Longitudinal Randomized Placebo-Controlled Trials", International Journal of Neuopsychopharmacology, 2015, pp. 1-7.
Folstein et al: "Mini-mental state: A practical method for grading the cognitive state of patients for the clinician", J. psychiat. Res., 1975, vol. 12, pp. 189-198.
Kvitting et al: "Age-Normative MMSE Data for Older Persons Aged 85 to 93 in a Longitudinal Swedish Cohort", JAGS, vol. 67 (3), 2019, pp. 534-538.
Wattmo et al: "Mild versus moderate stages of Alzheimer's disease: three-year outcomes in a routine clinical setting of cholinesterase inhibitor therapy", Alzheimer's Research & Therapy, vol. 8 (7), 2016.

\* cited by examiner

*Primary Examiner* — Snigdha Maewall
(74) *Attorney, Agent, or Firm* — N.V. Nederlandsch Octrooibureau

(57) ABSTRACT

The invention pertains to the use of therapeutically effective amounts of (a) (i) vitamin C and/or selenium and (ii) at least one of docosahexaenoic acid (22:6; DHA), eicosapentaenoic acid (20:5; EPA) and docosapentaenoic acid (22:5; DPA), or esters thereof; or (b) (i) vitamin C and/or selenium and (iii) one or more of uridine and cytidine, or salts, phosphates, acyl derivatives or esters thereof; or (c) a combination of (i), (ii) and (iii); wherein (a), (b) or (c) optionally further comprises vitamin E, in the manufacture of a product for therapeutically improving synaptic connectivity and/or therapeutically supporting memory and/or cognitive function in a human subject in need thereof.

13 Claims, 4 Drawing Sheets

METHOD FOR SUPPORTING MEMORY FUNCTION AND/OR COGNITIVE FUNCTION

The invention is in the field of medical nutrition and more particularly relates to a composition for use in supporting memory and/or cognitive function, improving or preserving synaptic connectivity and/or improving or preserving the brain network organization of a subject in need thereof; the composition is in particular for use in in adults, preferably elderly, for use in treating or preventing or reducing the risk of brain atrophy or brain shrinkage.

BACKGROUND DESCRIPTION

The brain is a plastic organ. Both pre- and postnatally the brain undergoes rapid changes wherein brain connections are formed. Throughout life, the brain retains its plasticity and consequently new neurites and synapses are constantly formed. The hippocampi, where memories are stored in response to experiences, are exemplary for the brain's continuous adaptation and development.

Brain atrophy on the other hand, is a feature of the ageing brain, but also a common feature of many diseases affecting the brain, with the pattern and rate of progression of the atrophy being dependent on the disease involved. Brain atrophy or cerebral atrophy can be described as the loss of neurons and the connections in-between, causing shrinkage of the brain volume. Atrophy can be generalized, which means that all of the brain has shrunk, or it can be focal, affecting only a limited area of the brain and resulting in a decrease of the functions that area of the brain controls. Symptoms of significant brain atrophy include progressive cognitive and/or memory impairment involving multiple cognitive functions, otherwise known as dementia, seizures and aphasia, which is the disruption in the understanding or production of language or both.

Some degree of cerebral shrinkage occurs naturally with age; after the brain completes growth and attains its maximum mass at around age 25, it gradually loses mass with each decade of life, although the rate of loss is comparatively tiny until the age of 60, when approximately 0.5 to 1% of brain volume is lost per year. By age 75, the brain is an average of 15% smaller than it was at 25. Some areas of the brain may shrink more than others, like the hippocampus, which is involved in memory.

Studies of improved nutrition in Alzheimer patients has shown improved neurocognitive outcomes in intervention groups, but whether increased nutritional intake may prevent or slow down brain atrophy in healthy subjects, or subjects suffering from brain atrophy and who are at risk of cognitive and/or memory function impairment has not been adequately studied.

There is a need to further investigate whether dietetic and nutritional intervention helps improving and supporting memory and/or cognitive function in subjects in need thereof.

SUMMARY OF THE INVENTION

The inventors have observed that upon administering a combination or product comprising (a) (i) vitamin C and/or selenium and (ii) at least one of docosahexaenoic acid (22:6; DHA), eicosapentaenoic acid (20:5; EPA) and docosapentaenoic acid (22:5; DPA), or esters thereof; or (b) (i) vitamin C and/or selenium and (iii) one or more of uridine and cytidine, or salts, phosphates, acyl derivatives or esters thereof; or (c) a combination of (i), (ii) and (iii), where (a), (b) or (c) are optionally in combination with vitamin E, to a human subject, functional synaptic connectivity in a subject's brain can be improved and/or preserved and brain network organization can be preserved or improved using the composition of the invention, in particular memory and/or cognitive function can be supported in a subject in need thereof, in particular in healthy elderly and in a subject with brain atrophy.

The invention thus pertains to a combination of (i) and (ii); or (i) and (iii); or (i), (ii) and (iii), for therapeutic use in a subject in need of improving synaptic connectivity, preventing/treating or reducing the risk of brain atrophy, and improving memory and/or cognitive function, preferably at least preventing or treating or reducing brain atrophy. It is preferred that therapeutically effective amounts of (i) and (ii) or (i) and (iii) or (i), (ii) and (iii) are part of a composition to be administered to said human subjects. The invention also pertains to a (therapeutic) method for improving synaptic connectivity, preventing brain atrophy and improving memory and/or cognitive function, said method comprising administering (therapeutically) effective amounts of (i) and (ii); or (i) and (iii); or (i), (ii) and (iii) to said human subjects, preferably healthy subjects. Also, the invention pertains to the use of therapeutic amounts of (i) and (ii); or (i) and (iii); or (i), (ii) and (iii) in the manufacture of a composition or medicament (i.e. a product) for therapeutic use in human subjects with suspected or confirmed brain atrophy and subjects at risk of neurodegeneration and neurodegenerative disease.

The invention also pertains to a non-therapeutic method for supporting memory function and/or cognitive function in healthy adults, preferably elderly. The invention is particularly useful in elderly from 55 years onwards, preferably from 60 years onwards, with sub-clinical brain atrophy.

The present inventors surprisingly found, through clinical study, that administration of a composition containing (i) vitamin C and/or selenium and either one or more of uridine and cytidine, or salts, phosphates, acyl derivatives or esters thereof; (ii) at least one of docosahexaenoic acid (22:6; DHA), eicosapentaenoic acid (20:5; EPA) and docosapentaenoic acid (22:5; DPA), or esters thereof; and (iii) one or more of uridine and cytidine, or salts, phosphates, acyl derivatives or esters thereof, optionally in combination with vitamin E, showed a significant improvement in memory and cognitive function in patients having brain atrophy and a mini mental state exam score (MMSE) of 20 or higher (i.e. of 20-30). A decrease in the loss of hippocampus volume was determined in subjects treated with the composition according to the invention. Compliance and tolerability were very high and side effects were relatively low. The results of the clinical study are summarized in the examples section. Moreover. in vivo experiments in healthy rats show that administration of a composition according to the invention results in increased synaptogenesis.

LIST OF FIGURES

Figure 2A:
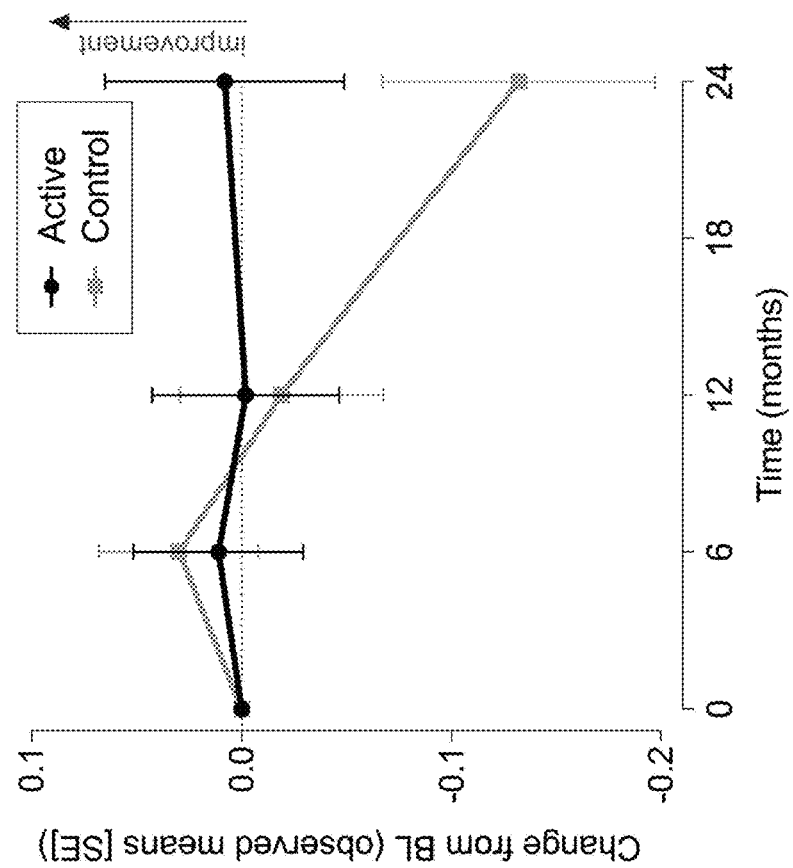
Figure 2B:
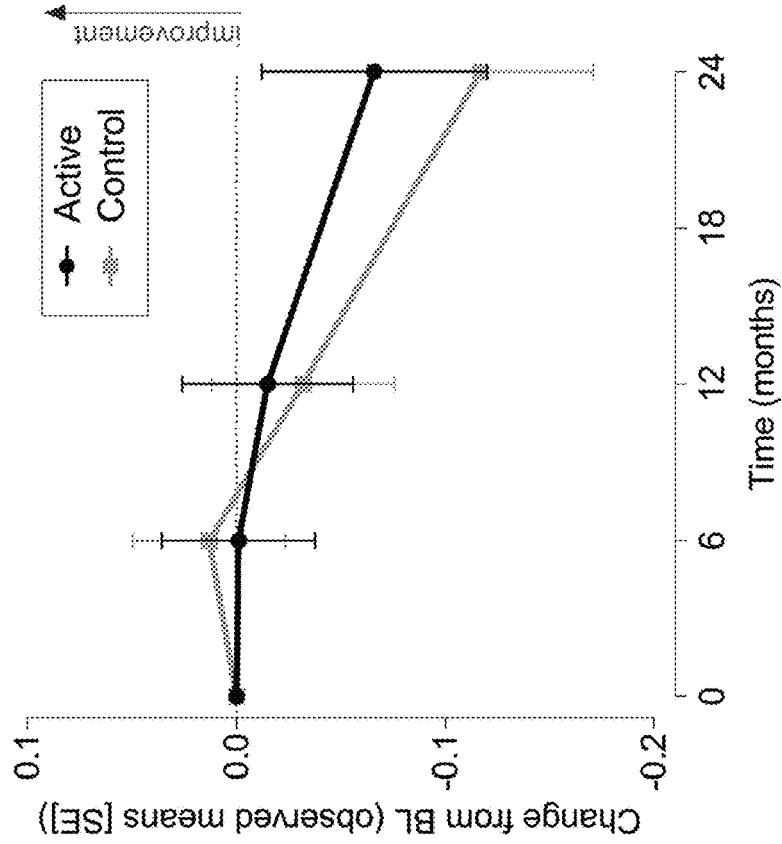

FIG. 2 shows the changes in cognitive function over time of a group of subjects having brain atrophy randomized to either control treatment or nutritional supplementation with a composition according to the present invention. A clinically relevant trend of decreased cognitive function loss is observed in the group that received the active composition according to the invention. FIG. 2A shows results for all randomised subjects, FIG. 2B shows the results for the per protocol population.

Figure 3A:
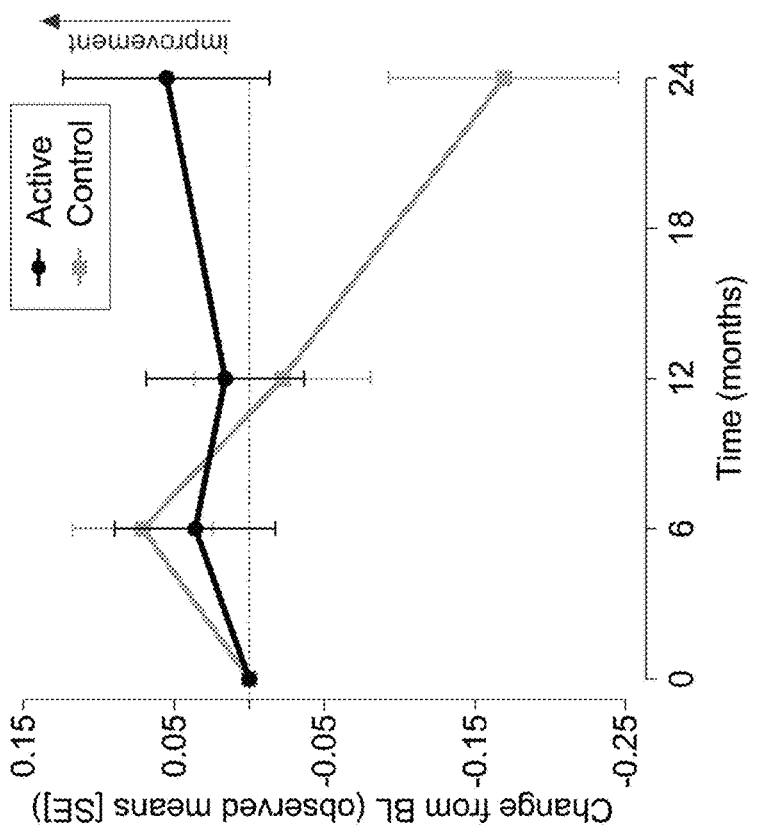
Figure 3B:
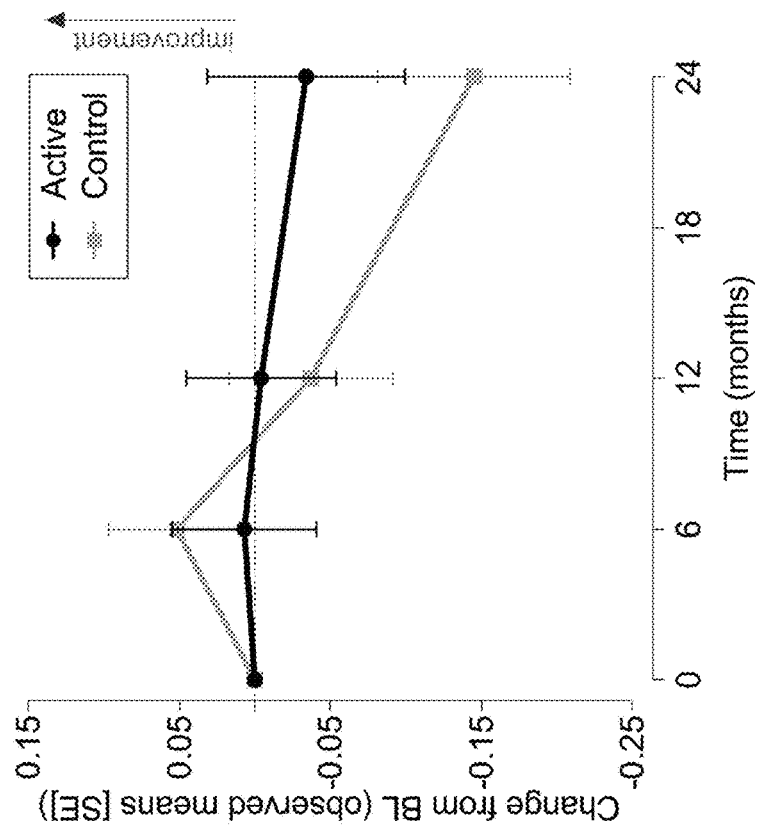
Figure 4:
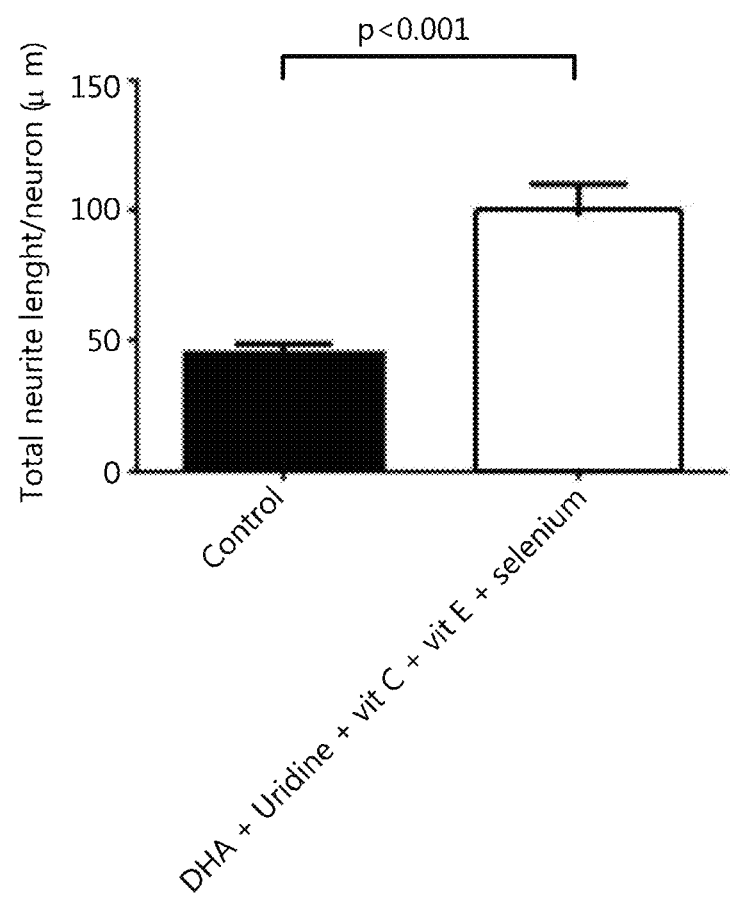

FIG. 3 shows the change in memory function of the same groups of subjects having brain atrophy and being randomized to either control treatment or nutritional supplementation with a composition according to the present invention over time. Slowing down of the decline in memory function was observed for the group that received the active composition. FIG. 3A shows results for all randomised subjects, FIG. 3B shows the results for the per protocol population FIG. 4 shows that a combination of DHA, uridine, Vitamin C, Vitamin E and selenium significantly ($p<0.0001$) improved neurite outgrowth (as measured as total neurite length per neuron) of PC12 cells in vitro.

LIST OF PREFERRED EMBODIMENTS

1. Use of therapeutically effective amounts of (a) (i) vitamin C and/or selenium and (ii) at least one of docosahexaenoic acid (22:6; DHA), eicosapentaenoic acid (20:5; EPA) and docosapentaenoic acid (22:5; DPA), or esters thereof; or (b) (i) vitamin C and/or selenium and (iii) one or more of uridine and cytidine, or salts, phosphates, acyl derivatives or esters thereof; or (c) a combination of (i), (ii) and (iii); wherein (a), (b) or (c) optionally further comprises vitamin E, in the manufacture of a product for therapeutically improving synaptic connectivity and/or therapeutically supporting memory and/or cognitive function in a human subject in need thereof.
2. Use according to embodiment 1, wherein a subject in need of therapeutically improving synaptic and/or therapeutically supporting memory and/or cognitive function is at increased risk of impaired cognitive and/or memory function.
3. Use according to embodiment 1 and 2, wherein the subject suffers from brain atrophy and/or is at risk of neurodegenerative disease.
4. Use according to any one of the preceding embodiments, wherein the product comprises therapeutic amounts of vitamin B6 and/or vitamin B12, including their functional equivalents.
5. Use according to any one of the preceding embodiments, wherein DHA is administered in an amount of at least 0.5 g per 100 g, preferably 0.5-5 g per 100 g of the product or per day.
6. Use according to any of the preceding embodiments, wherein uridine, as the cumulative amount of uridine, deoxyuridine, uridine phosphates, nucleobase uracil and acylated uridine derivatives, is administered in an amount of 0.1-5 g, preferably 0.2-2.5 g, more preferably 0.25-1 g per 100 g of the product or per day.
7. Use according to any of the preceding embodiments, wherein selenium is administered in an amount of 0.01-0.5 mg, preferably 0.02-0.1 mg per 100 g of the composition or per day.
8. Use according to any of the preceding embodiments, wherein vitamin C is administered in an amount of 20 to 1000 mg, in particular in the range of 30 to 500 mg, more in particular in the range of 50 to 150 mg per 100 g of the composition or per day.
9. A composition for use in therapeutically improving memory and/or cognitive function in a human subject in need thereof, said composition comprising (a) (i) vitamin C and/or selenium and (ii) at least one of docosahexaenoic acid (22:6; DHA), eicosapentaenoic acid (20:5; EPA) and docosapentaenoic acid (22:5; DPA), or esters thereof; or (b) (i) vitamin C and/or selenium and (iii) one or more of uridine and cytidine, or salts, phosphates, acyl derivatives or esters thereof; or (c) a combination of (i), (ii) and (iii); wherein (a), (b) or (c) optionally further comprises vitamin E.
10. A combination of therapeutically effective amounts of (i) vitamin C and/or selenium (ii) at least one of docosahexaenoic acid (22:6; DHA), eicosapentaenoic acid (20:5; EPA) and docosapentaenoic acid (22:5; DPA), or esters thereof; and (iii) one or more of uridine and cytidine, or salts, phosphates, acyl derivatives or esters thereof; wherein the combination optionally further comprises vitamin E, for use in therapeutically improving memory function and/or cognitive function in a human subject.
11. A method for (non-therapeutically) improving memory function and/or cognitive function in a healthy human subject in need thereof, said method comprising administering said subject with (a) (i) vitamin C and/or selenium and (ii) at least one of docosahexaenoic acid (22:6; DHA), eicosapentaenoic acid (20:5; EPA) and docosapentaenoic acid (22:5; DPA), or esters thereof; or (b) (i) vitamin C and/or selenium and (iii) one or more of uridine and cytidine, or salts, phosphates, acyl derivatives or esters thereof; or (c) a combination of (i), (ii) and (iii), wherein (a), (b) or (c) optionally further comprises vitamin E.
12. Method according to embodiment 11, wherein a subject in need of improving memory and/or cognitive function is at increased risk of impaired cognitive and/or memory function.
13. Method according to embodiment 11 and 12, wherein vitamin C is administered in an amount of 20 to 1000 mg, in particular in the range of 30 to 500 mg, more in particular in the range of 50 to 150 mg per 100 g of the composition or per day.
14. Method according to any of the embodiments 11 to 13, wherein uridine, as the cumulative amount of uridine, deoxyuridine, uridine phosphates, nucleobase uracil and acylated uridine derivatives, is administered in an amount of 0.1-5 g, preferably 0.2-2.5 g, more preferably 0.25-1 g per 100 g of the product or per day.
15. Method according to any of the embodiments 11 to 14, wherein selenium is administered in an amount of 0.01-0.5 mg, preferably 0.02-0.1 mg per 100 g of the composition or per day.
16. Method according to any of the embodiments 11 to 15, wherein DHA is administered in an amount of at least 0.5 g per 100 g, preferably 0.5-5 g per 100 g of the product or per day.

DETAILED DESCRIPTION OF THE INVENTION

Throughout this application, the following terminology and abbreviations may be used:

Brain atrophy of cerebral atrophy is characterized by gradual loss of brain volume and loss of synapse connectivity. In the process of ageing the brain shrinks. The extend of brain atrophy is generally determined using MRI wherein the volume of the brain and specific brain regions is determined. Hippocampus atrophy refers to atrophy in the medial temporal brain region where the hippocampi are located. Hippocampal atrophy is usually accompanied by deficits in declarative, episodic, spatial and contextual memory performance, with a reliable relationship between the size of the hippocampus and memory function performance. Hippocampal atrophy is a key feature of both hippocampal sclerosis (HS) and Alzheimer's disease (AD).

Elderly are human subjects preferably above the age of 55 years, preferably above 60 years.

Synaptic connectivity refers to connections formed between different neurons allowing transmission of signals between said neurons. The synapse plays a role in the formation of memory. Synaptogenesis is the formation of new synapses and synaptic connections.

Several diseases are causally linked to the development of brain atrophy. Atrophy may be caused by or associated with Alzheimer's disease, Cerebral palsy, Senile dementia, fronto-temporal dementia, and vascular dementia, Pick's disease, Huntington's disease, and other genetic disorders that cause build-up of toxic levels of proteins in neurons, Parkinson's disease and malnutrition. In those embodiments, the invention pertains to brain atrophy (prophylactic) treatment of human subjects suffering from the aforementioned disorders, particularly Alzheimer's disease, Cerebral palsy, Senile dementia, fronto-temporal dementia, and vascular dementia, Pick's disease, Huntington's disease and Parkinson's disease.

Medial temporal lobe atrophy (MTA) score refers to a visual score determined on coronal T1w MRI images through the hippocampus at the level of the anterior pons and assesses 3 features: 1) width of the choroid fissure, 2) width of the temporal horn of the lateral ventricle and 3) height of the hippocampus, resulting in a score of 0 to 4 depending on the degree of widening of the choroid fissure, enlargement of the temporal horn and atrophy of the hippocampus., wherein a score≥2 is considered abnormal in people under the age of 75 years.

The term 'memory function' describes a set of abilities that allows a subject to retrieve information that is no longer present. Memory is part of a subject's cognitive functioning.

In particular, memory is an organism's mental ability to store, retain and recall information. Memory phenomena that can be examined include: (1) knowledge (what to remember), (2) comprehension (what does it mean); (3) context/function (why to remember); and (4) strategy (how to remember). Memory is a complex psychological process that is not independent of a single memory domain process. Memory is related to several other cognition domains including, sensory memory, audio memory and visual memory Cognitive function refers to mental actions or processes of acquiring knowledge and understanding through thoughts, experience and the senses. Cognition encompasses processes such as knowledge, attention, memory and working memory, judgement, evaluation, reasoning, decision making, comprehension and production of language.

Mini mental state exam (MMSE) refers to a 30 point questionnaire to measure cognitive impairment such as in the diagnosis and longitudinal assessment of Alzheimer's disease. Any score greater than or equal to 24 points (out of 30) indicates a normal cognition. Below this, scores can indicate severe (≤9 points), moderate (10-18 points) or mild (19-23 points) cognitive impairment. The raw score may be corrected for educational attainment and age.

NTB test refers to a Neuropsychological Test Battery which comprises a combination of several validated, cognitive tests, yielding measures of a subjects performance in the cognitive field. The NTB tests were used to assess memory function and cognitive function.

In one aspect of the present invention, it pertains to a composition or combination with (i) and (ii); or (i) and (iii); or (i), (ii) and (iii), which may be used as a pharmaceutical product comprising one or more pharmaceutically acceptable carrier materials. In any case, the composition or combination may further comprise vitamin E.

In a preferred aspect of the present invention, (i) and (ii); or (i) and (iii); or (i), (ii) and (iii), are part of a composition which is used as a nutritional product, for example as a nutritional supplement, e.g., as an additive to a normal diet, as a fortifier, to add to a normal diet, or as a complete nutrition. The nutritional product preferably comprises at least one component selected from the group of fats, proteins, and carbohydrates. It preferably comprises between 30-60 en % carbohydrates, between 30 and 60 en % fat, and between 1 and 20 en % protein. It is understood that a nutritional product differs from a pharmaceutical product by the presence of nutrients which provide nutrition to the subject to which the composition is administered, in particular the presence of protein, fat, digestible carbohydrates and dietary fibres. It is preferably a composition complying with food for special medical purposes requirements, preferably according to EC directive FSMP 1999/21/EC which is herewith incorporated by reference. It may further contain ingredients such as minerals, vitamins, organic acids, and flavouring agents.

A first aspect of the invention provides for therapeutically improving memory function and/or cognitive function of human subjects having brain atrophy, which subjects may be at risk of neurodegenerative disease, by feeding said subject with:
(a) (i) vitamin C and/or selenium and (ii) at least one of docosahexaenoic acid (22:6; DHA), eicosapentaenoic acid (20:5; EPA) and docosapentaenoic acid (22:5; DPA), or esters thereof, or
(b) (i) vitamin C and/or selenium and (iii) one or more of uridine and cytidine, or salts, phosphates, acyl derivatives or esters thereof, or
(c) a combination of (i), (ii) and (iii),
where (a), (b) or (c) are optionally used in combination with vitamin E. The components are preferably provided in therapeutically effective amounts.

Another aspect of the invention provides for non-therapeutically improving memory function and/or cognitive function of human subjects, preferably adults, more preferably elderly, in need thereof, said subjects being in healthy condition, by feeding said subjects with:
(a) (i) vitamin C and/or selenium and (ii) at least one of docosahexaenoic acid (22:6; DHA), eicosapentaenoic acid (20:5; EPA) and docosapentaenoic acid (22:5; DPA), or esters thereof, or
(b) (i) vitamin C and/or selenium and (iii) one or more of uridine and cytidine, or salts, phosphates, acyl derivatives or esters thereof, or
(c) a combination of (i), (ii) and (iii),
where (a), (b) or (c) are optionally used in combination with vitamin E.

The invention is preferably for use in the support of memory and/or cognitive function of such healthy individuals.

In a preferred embodiment, the method of the invention is a method of therapeutically treating or preventing cognitive and/or memory dysfunction, preferably treating or preventing a decline or impairment in cognitive and/or memory function of a subject, in particular a subject with brain atrophy, in particular a subject with brain atrophy at risk of neurodegenerative disease. Prophylactic treatment includes reducing the risk of occurrence of a decline or impairment in cognitive and/or memory function. In an embodiment of the invention the subject with brain atrophy may be at risk of or suffering from prodromal Alzheimer's disease. The subject may be an elderly person.

The subject is a human subject, preferably an adult, more preferably an elderly person, preferably at least 55 years of age. Preferably, the subject has a mini-mental state examination (MMSE) score equal to or above 24, in particular equal or above 26, more particularly equal or above 27.

In yet another preferred embodiment, the method of the invention is a (non-therapeutic) method of supporting cognitive and/or memory function and/or improving synaptic connectivity in a subject in need thereof, the method is of particular use for human subjects wherein the brain is developing.

In yet another preferred embodiment, the method of the invention is a method of supporting cognitive and/or memory function and/or improving synaptic connectivity in a subject in need thereof and of particular use for a subject with brain atrophy at risk of memory and/or cognitive impairment.

Effective amounts of the composition according to the invention result in improved memory and/or cognitive function. In yet a further embodiment the effective amount of the composition according to the invention result in increased synaptogenesis in said subjects in need thereof, more preferably results in physiological increases in brain volume and hippocampus volume.

In yet another preferred embodiment the method and composition for use according to the invention are of particular use for healthy subjects, more preferably elderly. Effective amounts of the composition are for use in said subjects.

In one embodiment, with 'preventing' it is intended to mean that the drop in cognitive and/or memory functions is lower with the use of the composition according to the invention compared to a control group of treatment-naïve subjects suffering from the same condition but not given the composition of the invention.

According to one embodiment of the invention, the composition is provided as a nutritional product or nutritional supplement. The product of the invention is an enteral composition, intended for oral administration. It is preferably administered in liquid form. In one embodiment, the food product is a liquid composition containing between 50 and 250 kcal per 100 ml, more preferably between 75 and 125 kcal per 100 ml.

Preferably, the composition is enterally administered to the patient at least one time per day for a period of at least 12 weeks, preferably at least 26 weeks, more preferably at least 1 year, or at least 2 years.

The method or use of the invention comprises administering (therapeutically) effective amounts of the composition comprising the aforementioned ingredients(i)-(ii) or (i)-(iii) or (i)-(ii) and (iii), and as outlined above, to a subject in need thereof. The prophylactic or preventive aspect includes reducing the risk of occurring of memory and cognitive impairment.

ω-3 LC-PUFAs

The method, composition or combination of the invention comprise (therapeutically) effective amounts of at least one omega-3 long-chain polyunsaturated fatty acid (LC PUFA; having a chain length of 18 and more carbon atoms) selected from the group consisting of docosahexaenoic acid (22:6; DHA), eicosapentaenoic acid (20:5; EPA) and docosapentaenoic acid (22:5 ω-3; DPA), preferably at least one of DHA and EPA. Preferably the present composition or combination contains at least DHA, more preferably DHA and EPA. EPA is converted to DPA (ω-3), increasing subsequent conversion of DPA to DHA in the brain. Hence, the present composition or combination preferably also contains a significant amount of EPA, so to further stimulate in vivo DHA formation.

The LCPUFAs (DHA, EPA and/or DPA) are preferably provided as triglycerides, diglycerides, monoglycerides, free fatty acids or their salts or esters, phospholipids, lysophospholipids, glycerol ethers, lipoproteins, ceramides, glycolipids or combinations thereof. Preferably, the present composition or combination comprises at least DHA in triglyceride form. Suitable ω-3 LCPUFA and/or DHA sources include tuna oil, (other) fish oils, DHA-rich alkyl esters, algae oil, egg yolk, or phospholipids enriched with ω-3 LCPUFA e.g. phosphatidylserine-DHA. Preferably, a composition or combination according to the invention comprises fish oil providing the omega-3 LCPUFA(s). Another particularly suitable source for the omega-3 LCPUFA(s) is algae oil.

If EPA, DHA and/or EPA are present, the total daily dosage of DHA+EPA+DPA taken together is in the range of 0.25-5 g, preferably 0.5-5 g, more preferably 0.75-2.5 g, per 100 g of the composition, or in terms of daily dosage, in the range of 0.25-5 g, preferably 0.5-5 g, more preferably 0.75-2.5 g, per day. In a preferred embodiment, these amounts are based on the total sum of DHA and EPA if present. DHA is preferably administered in therapeutic amounts, preferably in an amount of at least 0.5 g per 100 g, more preferably 0.5-5 g per 100 g, most preferably 0.75-2 g per 100 g of the composition, or in terms of daily dosage, in the range of at least 0.5 g per 100 g, more preferably 0.5-5 g per 100 g, most preferably 0.75-2 g per day.

In terms of the composition, combination or method, the proportion of ω-3 LCPUFA (more preferably DHA+EPA+DPA, most preferably DHA+EPA) of the total fatty acids in the composition is preferably 5 to 95 wt %, more preferably 10 to 80 wt %, most preferably 15 to 70 wt %, even more preferably 20 to 60 wt % of the total fatty acids. The present composition or combination preferably comprises 5 to 95 wt % DHA based on total fatty acids, preferably 10 to 75 wt % DHA based on total fatty acids, more preferably 10 to 60 wt %, even more preferably 10-50 wt %, more preferably 10-40 wt %, especially at least 20 wt % DHA, based on total fatty acids of the composition or combination. The present composition or combination preferably comprises 5 to 95 wt % EPA based on total fatty acids, preferably 5 to 75 wt % EPA, even more preferably 5-50 wt %, more preferably 5-25 wt %, most preferably 5-15 wt %, based on total fatty acids of the composition or combination.

In the method, combination or composition of the invention, the ratio of the weight of DHA to EPA is preferably larger than 1, more preferably 2:1 to 10:1, more preferably 2:1 to 5:1. The ratios take into account and optimize the balance between DHA and precursors thereof to ensure optimal effectiveness while maintaining low-volume formulations.

If arachidonic acid (AA) is present or administered, it concerns a very low amount of AA, expressed in terms of a DHA/AA weight ratio in the present composition, combination or method of at least 5, preferably at least 6. If AA is administered, it preferably amounts to less than 5 g per 100 ml liquid product and/or less than 300 mg per 100 g dry weight of the composition or combination.

Uridine, Cytidine and/or Equivalents thereof

The method, combination and composition according to the invention comprise (therapeutically) effective amounts of one or more of uridine, cytidine and/or an equivalent thereof, including salts, phosphates, acyl derivatives and/or esters. The method, combination and composition preferably comprises at least one uridine or an equivalent thereof selected from the group consisting of uridine (i.e. ribosyl uracil), deoxyuridine (deoxyribosyl uracil), uridine phosphates (UMP, dUMP, UDP, UTP), nucleobase uracil and acylated uridine derivatives. In one embodiment, cytidine, CMP, citicoline (CDP-choline) may also be applied in addition to or instead of uridine (equivalent). Preferably, the composition or combination to be administered according to the present invention comprises a source of uridine selected from the group consisting of uridine, deoxyuridine, uridine phosphates, uracil, and acylated uridine.

Preferably, the method, combination and composition according to the invention comprise an uridine phosphate selected from the group consisting of uridine monophosphate (UMP), uridine diphosphate (UDP) and uridine triphosphate (UTP); and/or a cytidine phosphate (CMP, CDP, CTP, preferably CMP). In a preferred embodiment, the composition or combination comprises at least one of the aforementioned uridine phosphates. Most preferably the present composition or combination comprises UMP, as UMP is most efficiently being taken up by the body. Hence, inclusion of UMP in the present method, combination and composition enables a high effectivity or efficacy at the lowest dosage and/or the administration of a low volume to the subject. Preferably at least 50 weight % of the uridine in the present method, combination and composition is provided by UMP, more preferably at least 75 weight %, most preferably at least 95 weight %. Doses administered are given as UMP. The amount of uracil sources can be calculated taking the molar equivalent to the UMP amount (molecular weight 324 Dalton).

The present method preferably comprises the administration of uridine (the cumulative amount of uridine, deoxyuridine, uridine phosphates, nucleobase uracil and acylated uridine derivatives) in an amount of 0.1-5 g, preferably 0.2-2.5 g, more preferably 0.25-1 g per 100 g of the composition, or in terms of daily dosage, in the range of 0.1-5 g, preferably 0.2-2.5 g, more preferably 0.25-1 g per day. In one embodiment, the present method, combination and composition may comprise the administration a uridine source in a concentration of 0.1-5 g, preferably 0.2-2.5 g, more preferably 0.25-1 g per, calculated as UMP, per 100 kcal product. The terms product, composition and combination are used interchangeably.

Vitamin C, Selenium and vitamin E

The method, combination and composition according to the invention comprise (therapeutically) effective amounts of vitamin C and/or selenium, optionally in combination with vitamin E. It is especially preferred that the composition comprises both vitamin C and selenium, and optionally further comprises vitamin E, most preferably the composition according to the invention comprises vitamin C, vitamin E and selenium.

Vitamin C includes functional equivalents thereof, and may be present in an amount in the range of 20 to 1000 mg, in particular in the range of 30 to 500 mg, more in particular in the range of 50 to 150 mg per 100 g of the composition, or in terms of daily dosage, in the range of 20 to 1000 mg, in particular in the range of 30 to 500 mg, more in particular in the range of 50 to150 mg per day.

Selenium may be present in an amount of 0.01-0.5 mg, preferably 0.02-0.1 mg per 100 g of the composition, or in terms of daily dosage, in the range of 0.01-0.5 mg, preferably 0.02-0.1 mg per day.

Vitamin E refers to compounds having vitamin E activity as known in the art, typically tocopherol and/or an equivalent thereof. Vitamin E may be present as tocopherol and tocopherol equivalents in an amount in the range of 10 to 200 mg, in particular in the range of 10 to 100 mg, more in particular in the range of 20 to 50 mg per 100 g of the composition, or in terms of daily dosage, in an amount in the range of 10 to 200 mg, in particular in the range of 10 to 100 mg, more in particular in the range of 20 to 50 mg per day. The term 'tocopherol and equivalent thereof', as used in this description, comprises tocopherols (e.g. alpha- and gamma-), tocotrienols, pharmaceutical and/or nutritional acceptable derivatives thereof and any combination thereof. The above numbers are based on alpha-tocopherol equivalents (alpha-TE), as recognized in the art.

Choline

In a preferred embodiment, the method, combination and composition according to the present invention comprise (therapeutically) effective amounts of choline, a choline salt and/or choline ester. Herein, the term 'choline' shall be considered to encompass all these equivalents. Choline salts are preferred. The choline salt is preferably selected from choline chloride, choline bitartrate, or choline stearate. The choline ester is preferably selected from the group consisting of phosphatidylcholine and lyso-phosphatidylcholine. The present method preferably comprises the administration of more than 0.1 g choline per 100 g, preferably 0.1 to 1 g choline per 100 g, more preferably 0.2 to 0.5 g choline per 100 g of the composition or combination, or in terms of daily dosage, more than 0.1 g choline per 100 g, preferably 0.1 to 1 g choline per 100 g, more preferably 0.2 to 0.5 g choline per day. The above numbers are based on choline, the amounts of choline equivalents or sources can be calculated taking the molar equivalent to choline into account, based on the molar mass of 104 g/mol choline.

B Vitamins

In a preferred embodiment, the method, combination and composition according to the present invention comprise (therapeutically) effective amounts of at least one B vitamin selected from the group consisting of vitamin B6 (pyridoxine, pyridoxal, or pyridoxamine, or pyridoxine hydrochloride), vitamin B9 (folic acid or folate), and vitamin B12 (cobalamins). Functional equivalents are encompassed within these terms. Preferably the present composition comprises at least vitamin B6 and/or vitamin B9, more preferably at least vitamins B6 and B9, most preferably vitamins B6, B9 and B12. Vitamin B6 is preferably administered to provide an amount of 100-500 mcg, preferably 150-300 mcg, based on 100 g of the composition or per day. Vitamin B9 is preferably administered to provide an amount to provide 50 to 1000 jag, in particular in the range of 100 to 1000 µg, more in particular in the range of 200 to 800 µg per 100 g of the composition or per day. Vitamin B9 may be present as folate, which includes folic acid, folinic acid, methylated, methenylated and formylated forms of folates, their salts or esters (e.g. C1-6 alkyl ester), as well as their derivatives with one or more glutamic acid, and all in either reduced or oxidized form. Preferably, vitamin B9 is provided as folic acid. Vitamin B12 is preferably administered to provide an amount in the range of 0.5 to 20 jag, in particular in the range of 1 to 10 µg per 100 g of the composition or per day. The term "vitamin B12" incorporates all cobalbumin equivalents known in the art.

In a preferred embodiment, the method, combination and composition according to the present invention further comprises choline and at least vitamin B6 and/or vitamin B9, more preferably at least vitamins B6 and B9, most preferably vitamins B6, B9 and B12.

The composition may further comprise a digestible carbohydrate fraction, preferably including a source of lactose and a source of polysaccharide.

EXAMPLES

For a more complete understanding of the present disclosure, reference is now made to the following examples taken in conjunction with the accompanying drawings.

Example 1. Clinical Trial

A randomised, controlled, double-blind, parallel-group, multi-country clinical study was undertaken wherein 311 prodromal subjects were either treated for 2 years with a composition according to the invention (active composition, per 125 ml: 300 mg EPA, 1200 mg DHA, 106 mg phospholipids, 400 mg choline, 625 mg UMP, 40 mg vitamin E, 80 mg vitamin C, 60 mcg selenium, 3 mcg vitamin B12, 1 mg vitamin B6, 400 mcg folic acid) or received an iso-caloric control.

Inclusion criteria for prodromal patients were defined as follows:
1) suffering from episodic memory disorder, defined as −1 SD on 2 out of 8 tests (further explained below) of which at least memory test score is −1 SD.
2) Evidence for underlying Alzheimer's disease pathology
   Medial temporal lobe atrophy≥1 determined on MRI images
   Cerebral spinal fluid measurement of: β-amyloid ratio<1 or p-tau>60 or t-tau>350, or,
   An abnormal FDG-PET compatible with Alzheimer's disease type of changes.
3) Age between 55-85 years
4) MMSE≥24 (≥20 for subjects with ≤6 years of formal education)
5) Informed consent from both the subject as well as a caregiver.

A total of 311 subjects were randomized into either the iso-caloric (itt n=158) or the active composition (itt n=153) group.

Figure 1A:
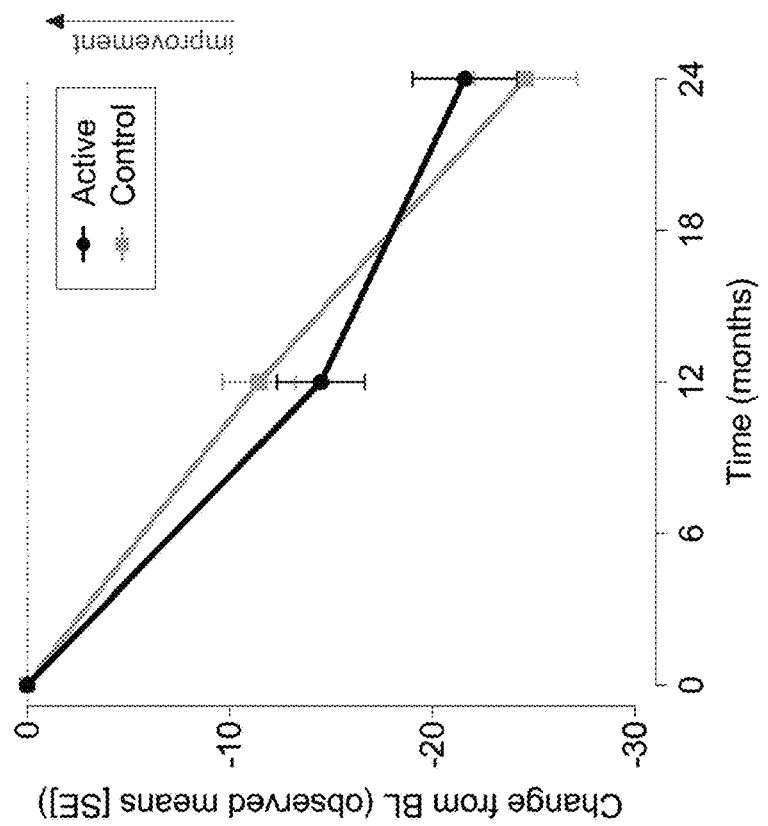
FIG. 1A shows the changes in total hippocampal volume in cm 3 over time of a group of subjects having brain atrophy randomized to either control treatment or nutritional supplementation with a composition according to the present invention. A significant slowing of hippocampus (left and right) atrophy was observed in the group that received the active composition.

The tests mentioned in the inclusion criteria are the following:
Memory
   FCSRT—delayed free recall*≤8
   FCSRT free recall—learning≤22
   WMS-R story delayed recall (%)≤75%
   WMS-R delayed recall of figures (%)≤75%
Non-Memory
   TMT A≥60
   TMT B≥150
   Symbol Digit Substitution Test≤35 (120 sec.)
   Category Fluency≤16 (60 sec.)
Abbreviations:
   FCRT: Free and Cued Selective reminding test, WMS: Wechsler Memory Scale, TMT: Trial Making Test FIG. 1A shows the changes in total hippocampal volume in $cm^3$ over time. Significant slowing of left and right hippocampus atrophy was observed in the active group (left: p=0.052; right: p=0.016, data not shown). A significant slowing of total hippocampus (left and right) atrophy was observed in the group that received the active composition, MM slope p=0.011 in the itt group comprising all randomised subjects. (MM*24 months p-0.008)

Figure 1B:
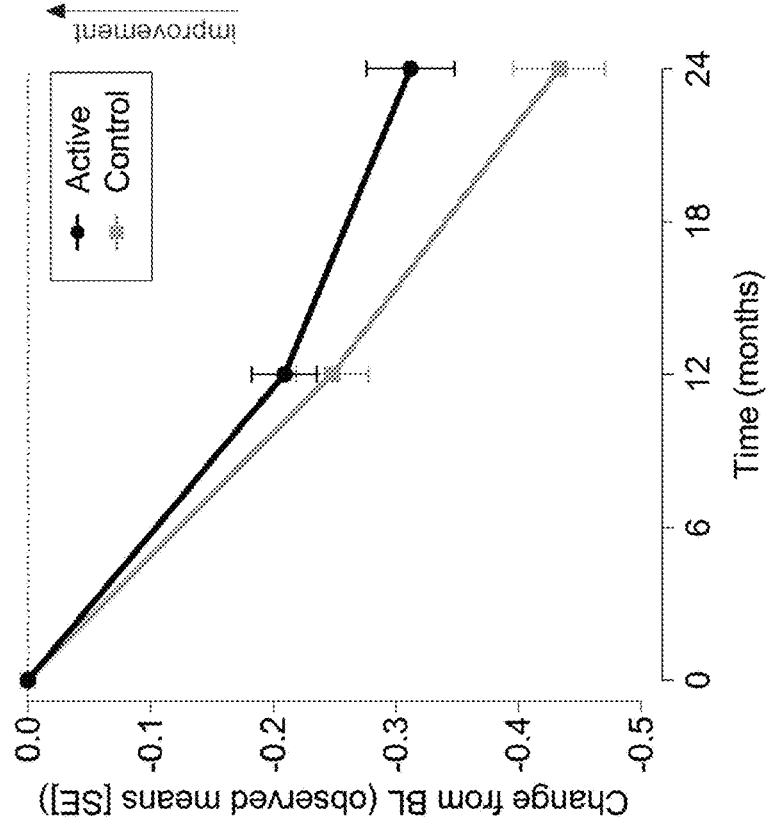
FIG. 1B shows the changes in total brain volume in $cm^3$ over time of a group of subjects having brain atrophy randomized to either control treatment or nutritional supplementation with a composition according to the present invention. Slowing of brain atrophy was observed in the group that received the active composition.

FIG. 1B shows the changes in total brain volume in $cm^3$ over time. Slowing of total brain atrophy was observed in the group that received the active composition (MM slope p=0.033, MM*24 months p=0.416 and ANCOVA 24 months p=0.420) for the itt group comprising all randomised subjects.

FIG. 2 shows the changes in cognitive function over time. To assess cognitive function Z-scores were calculated based on at least 4 out of 5 NTB tests relevant for cognitive function (CERAD immediate & delayed recall & recognition, Category Fluency, LDST). The calculation was performed for each of the NTB components by subtracting the baseline mean of the item (over the entire ITT population) and dividing by the baseline SD of the item (over the entire ITT population). The resultant z-scores were averaged to obtain the composite z-score. A clinical relevant trend of decreased cognitive function loss is observed in the group that received the active composition according to the invention. FIG. 2A shows the itt group with all randomised subjects, FIG. 2B shows the per protocol analysed subjects.

FIG. 3 shows the change in memory function of the same groups of subjects over time. The memory composite Z-scores were calculated based on the performance of a subject in 3 NTB components (CERAD immediate & delayed recall & recognition). The calculation was performed for each of the NTB components by subtracting the baseline mean of the item (over the entire ITT population) and dividing by the baseline SD of the item (over the entire ITT population). The resultant z-scores were averaged to obtain the composite z-score. The memory domain Z-score was only calculated if all 3 NTB components were available. Slowing of the decline in memory function was observed for the group that received the active composition. Treatment adherence during the study period was >90% for both groups and the study protocol was generally well tolerated without severe adverse effects being reported in either treatment group. FIG. 3A shows the itt group with all randomised subjects, FIG. 3B shows the per protocol analysed subjects.

Overall a clear benefit was observed for the group of subjects that were randomized into the group receiving the active composition according to the invention, with a slower development of hippocampal and total brain atrophy and a slower decline in memory and cognitive function.

Example 2. Effect of Exposure of Healthy Rats to the Composition of the Invention on Synapses The additional value of vitamin C, vitamin E and selenium according to the invention was assessed in healthy rats supplemented with uridine (as uridine-5'-monophosphate) and fish oil (FO), containing DHA and EPA.

Rats were randomized to four treatment groups and fed 1 of the 4 intervention diets for 6 weeks (see Table 1). On completion of dietary treatment, rats were sacrificed, and brain samples were analyzed for levels of phospholipids, synaptic proteins, and 2 enzymes that are involved in the synthesis of phospholipids, i.e. choline-phosphate cytidylyltransferase (PCYT1A) and choline/ethanolamine phosphotransferase (CEPT1).

TABLE 1

Diets comprising different amounts of the antioxidants, fish oil and UMP.

| | Diet (grams/100 gram diet) | | | |
|---|---|---|---|---|
| Nutrient | Diet 1 antioxidant low | Diet 2 antioxidant high | Diet 3 antioxidant low & fish oil + UMP | Diet 4 antioxidant high & FO + UMP |
| Vitamin C | 0 | 0.160 | 0 | 0.160 |
| Vitamin E | 0.000385 | 0.160 | 0.000385 | 0.160 |
| Selenium | 0.000007 | 0.00012 | 0.000007 | 0.00012 |
| Fish oil | — | — | 3.2 | 3.2 |
| UMP | — | — | 1.0 | 1.0 |

Levels of total and individual phospholipids (except for phosphatidylinositol), levels of the pre- and post-synaptic proteins Synapsin-1 and PSD-95, as well as the levels of the enzymes PCYT1A and CEPT1, were all significantly increased by combined supplementation of fish oil plus uridine and antioxidants, and levels were not enhanced by supplementation of fish oil plus uridine without antioxidants. See table 2 for results.

TABLE 2

Effects of specific dietary intervention with antioxidants, fish oil and UMP in rats on brain levels of phospholipids, synaptic proteins, and enzymes involved in phospholipids synthesis.

| | Dietary intervention | | | |
|---|---|---|---|---|
| Brain Levels | antioxidant low | antioxidant high | antioxidant low & fish oil + UMP | antioxidant high & fish oil + UMP |
| Total phospholipids (nmol/mg protein) | 365.9 ± 15.7 | 363.4 ± 18.1 | 392.5 ± 21.5 | 457.7 ± 17.8* |
| PC (nmol/mg protein) | 136.6 ± 3 | 135.9 ± 3.1 | 148.6 ± 4.04 | 166.9 ± 4.7* |
| PE (nmol/mg protein) | 93.9 ± 3.7 | 93.9 ± 4.5 | 102.1 ± 5.2 | 120.8 ± 4.8* |
| PS (nmol/mg protein) | 30.5 ± 1.4 | 30.5 ± 1.4 | 33 ± 2 | 39.2 ± 1.7* |
| SM (nmol/mg protein) | 19.7 ± 0.7 | 19.6 ± 1 | 20.3 ± 1.2 | 24 ± 0.8* |
| PI (nmol/mg protein) | 17.7 ± 1.8 | 17.2 ± 1.7 | 17.9 ± 1.4 | 21.3 ± 1.5 |
| PSD-95 (% of AOX low values) | 100 ± 1.8 | 107.3 ± 3.8 | 115.9 ± 5.2 | 132.9 ± 5.9* |
| Synapsin-1 (% of AOX low values) | 100 ± 1.8 | 106.6 ± 3.1 | 113.1 ± 6.3 | 136.6 ± 6.1* |
| b-Tubulin control protein (% of AOX low values) | 100 ± 2.7 | 95.9 ± 3.7 | 95.1 ± 3.4 | 108.4 ± 5.6 |
| Brain PCYT1A (ng/mL) | 9.5 ± 0.1 | 9.9 ± 1 | 9.9 ± 0.1 | 12.4 ± 0.2* |
| Brain CEPT1 (ng/mL) | 11.4 ± 0.2 | 12.04 ± 0.2 | 12.06 ± 0.1 | 14.01 ± 0.2* |

Values are mean ± SEM. *P < 0.05 vs. AOX low, One-way ANOVA post hoc comparison.

The results show that the antioxidants, vitamin C, vitamin E and selenium, in a diet containing phospholipid precursors exert a synergistic effect for the precursors' effects on increasing levels of both membrane phospholipids and synaptic proteins, the indirect indicators of neurite formation synaptogenesis and synaptic connectivity. Moreover, levels of the enzymes involved in phospholipid synthesis were also increased when the combination was supplemented and not by supplementing either FO plus uridine or AOX alone.

Example 3: In Vitro Study of the Effect of a Composition According to the Invention on Neuron Outgrowth PC12 pheochromocytoma cells were grown in DMEM (Gibco), supplemented with 10% fetal bovine serum (FBS), penicillin (100 units/ml), and streptomycin (100 µg/ml) (Gibco), under a humidified atmosphere with 95% air and 5% $CO_2$ at 37° C. Cells were seeded in a 96 well plates at a density of 2000 cells/well, and after 24 hours supplemented with medium containing 20 ng/ml nerve growth factor (NGF). The cells were exposed to either a composition according to the invention or left unsupplemented (control). The composition the cells were supplemented with is indicated in table 3. Supplementation of cells was performed in triplicate. These conditions were compared to nonsupplemented cells. After supplementation for 2 days with these combinations, cells were stained using Calcein-AM stain (2 ng/microliter) and the nuclei were counterstained using Hoechst stain (0.6 microgram/ml), in 100 µl culture medium per well and incubated for 20-30 min at 37° C. Subsequently, FITC and DAPI images (25 images per well) were taken using an Arrayscan XTI high content imaging system. Neurite outgrowth was quantified using the Neuronal profiling Bioapplication algorithm. Finally, all data were statistically analyzed using Graphpad Prism. The present data show that a combination of DHA, uridine, Vitamin C, Vitamin E and selenium significantly ($p<0.0001$) improved neurite outgrowth (as measured as total neurite length per neuron) of PC12 cells in vitro (FIG. 4).

Brain functioning, ranging from perception and motor control to cognition, heavily depends on the structural connectivity between neurons that supports coordinated activity in neuronal networks. At the cellular level, the shape of a neuron (e.g. neurite length, and number of neurites and branches) is critical for its function as it determines the number of inputs the neuron can receive and how those inputs are processed. The results obtained with PC12 cells exposed to the composition according the invention is indicative of new neurite formation in response to the composition according to the invention.

TABLE 3

PC12 cells were supplemented with a composition comprising the nutrient DHA, uridine, vitamin C, vitamin E and selenium for 2 days.

| Nutrient | Concentration (μM) |
|---|---|
| DHA | 15 |
| Uridine | 75 |
| Vitamin C | 225 |
| Vitamin E | 60 |
| Selenium | 0.24 |

Example 4. A Liquid Composition According to the Invention, Comprising Per 125 mL Serving

| | |
|---|---|
| 4.9 g fat | 40 mg vitamin E (alpha-TE) |
| 300 mg EPA | 80 mg vitamin C |
| 1200 mg DHA | 60 μg selenium |
| 106 mg phospholipids | 3 μg vitamin B12 |
| 400 mg choline | 1 mg vitamin B6 |
| 625 mg UMP | 400 μg folic acid |

The invention claimed is:

1. A method for treating or reducing the risk of brain atrophy or brain shrinkage in a healthy elderly human subject with a mini-mental state examination (MMSE) score equal to or above 27, the method comprising administering to the subject a composition comprising
   (i) vitamin C, vitamin E and selenium; and
   (ii) at least docosahexaenoic acid (22:6; DHA), or esters thereof; and
   (iii) 0.1-5 g uridine or uridine monophosphate (UMP), per 100 g of the composition,
   wherein selenium is administered in an amount of 0.01-0.5 mg per 100 g of the composition or per day, wherein vitamin C is administered in an amount of 20 to 1000 mg per 100 g of the composition or per day and wherein vitamin E is administered in an amount of in the range of 20 to 50 mg per 100 g of the composition or per day.

2. The method according to claim 1, wherein the composition comprises (ii) DHA and eicosapentaenoic acid (20:5; EPA), or esters thereof.

3. The method according to claim 1, wherein the composition comprises therapeutic amounts of vitamin B6 and/or vitamin B12, including their functional equivalents.

4. The method according to claim 1, wherein DHA is administered in an amount of at least 0.5 g per 100 g of the composition or per day.

5. The method according to claim 1, wherein DHA is administered in an amount of 0.5-5 g per 100 g of the composition or per day.

6. The method according to claim 1, wherein vitamin C is administered in an amount of 30 to 500 mg per 100 g of the composition or per day.

7. The method according to claim 1, wherein vitamin C is administered in an amount of 50 to 150 mg per 100 g of the composition or per day.

8. A method for treating or reducing the risk of brain atrophy or brain shrinkage in a healthy elderly human subject with a mini-mental state examination (MMSE) score equal to or above 27, the method comprising administering to the subject a composition comprising:
   (i) vitamin C, vitamin E and selenium; and
   (ii) DHA and EPA, or esters thereof; and
   (iii) 0.1-5 g uridine per 100 g of the composition,
   wherein selenium is administered in an amount of 0.01-0.5 mg per 100 g of the composition or per day, wherein vitamin C is administered in an amount of 20 to 1000 mg per 100 g of the composition or per day and wherein vitamin E is administered in an amount of in the range of 20 to 50 mg per 100 g of the composition or per day.

9. The method according to claim 8, wherein the composition comprises therapeutic amounts of vitamin B6 and/or vitamin B12, including their functional equivalents.

10. The method according to claim 8, wherein DHA is administered in an amount of at least 0.5 g per 100 g of the composition or per day.

11. The method according to claim 10, wherein DHA is administered in an amount of 0.5-5 g per 100 g of the composition or per day.

12. The method according to claim 8, wherein vitamin C is administered in an amount of 30 to 500 mg per 100 g of the composition or per day.

13. The method according to claim 8, wherein vitamin C is administered in an amount of 50 to 150 mg per 100 g of the composition or per day.

* * * * *